US012247052B2

(12) United States Patent
Demuth et al.

(10) Patent No.: US 12,247,052 B2
(45) Date of Patent: Mar. 11, 2025

(54) CPG AMPHIPHILES AND USES THEREOF

(71) Applicant: Elicio Therapeutics, Inc., Cambridge, MA (US)

(72) Inventors: Peter C. Demuth, Medford, MA (US); Martin Steinbuck, Boston, MA (US)

(73) Assignee: Elicio Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/977,185

(22) PCT Filed: Mar. 1, 2019

(86) PCT No.: PCT/US2019/020398
§ 371 (c)(1),
(2) Date: Sep. 1, 2020

(87) PCT Pub. No.: WO2019/169328
PCT Pub. Date: Sep. 6, 2019

(65) Prior Publication Data
US 2021/0040159 A1    Feb. 11, 2021

Related U.S. Application Data

(60) Provisional application No. 62/637,824, filed on Mar. 2, 2018.

(51) Int. Cl.
| *A61K 38/16* | (2006.01) |
| *A61K 39/12* | (2006.01) |
| *A61K 39/39* | (2006.01) |
| *A61K 47/54* | (2017.01) |
| *C07H 21/04* | (2006.01) |
| *C07K 14/025* | (2006.01) |
| *A61K 38/00* | (2006.01) |
| *A61K 39/00* | (2006.01) |
| *A61K 45/06* | (2006.01) |

(52) U.S. Cl.
CPC .......... *C07K 14/025* (2013.01); *A61K 38/162* (2013.01); *A61K 39/12* (2013.01); *A61K 47/544* (2017.08); *C07H 21/04* (2013.01); *A61K 38/00* (2013.01); *A61K 39/0011* (2013.01); *A61K 45/06* (2013.01)

(58) Field of Classification Search
CPC .................. A61K 38/162; A61K 39/12; A61K 2039/55561; A61K 2039/80; C07K 14/025; C07H 21/04; C12N 15/00
See application file for complete search history.

(56) References Cited

U.S. PATENT DOCUMENTS

| 6,168,778 | B1 * | 1/2001 | Janjic ................. A61K 47/549 424/1.73 |
| 10,940,201 | B2 * | 3/2021 | Kugimiya ............. A61P 35/00 |
| 2007/0298449 | A1 * | 12/2007 | Saito ..................... A61P 37/04 435/29 |
| 2008/0299138 | A1 * | 12/2008 | Duffy .................... A61P 13/12 514/1.1 |
| 2012/0121606 | A1 | 5/2012 | Ruben et al. |
| 2012/0129199 | A1 | 5/2012 | Daftarian et al. |
| 2012/0264810 | A1 * | 10/2012 | Lin ...................... A61K 9/1271 514/44 A |
| 2012/0328701 | A1 * | 12/2012 | Edelson .................. A61P 1/04 424/490 |
| 2014/0162944 | A1 | 6/2014 | Tiberg et al. |
| 2014/0294932 | A1 | 10/2014 | Kim et al. |
| 2015/0044208 | A1 | 2/2015 | Castanheira Aires da Silva et al. |
| 2015/0232514 | A1 | 8/2015 | Dockal et al. |
| 2015/0283205 | A1 | 10/2015 | Phipps et al. |
| 2016/0000906 | A1 | 1/2016 | Diamond |
| 2016/0220669 | A1 | 8/2016 | Hoves et al. |
| 2016/0264810 | A1 * | 9/2016 | Okamoto ............... B22F 1/0022 |
| 2017/0246288 | A1 * | 8/2017 | Li ................... A61K 39/001191 |
| 2020/0061172 | A1 * | 2/2020 | Kulangara ......... A61K 39/0013 |
| 2021/0060149 | A1 * | 3/2021 | Demuth ............... A61K 47/544 |

FOREIGN PATENT DOCUMENTS

| RU | 2477315 C2 | 3/2013 |
| WO | WO-2006/134423 A2 | 12/2006 |
| WO | WO-2008/068638 A2 | 6/2008 |
| WO | WO-2010/008782 A1 | 1/2010 |
| WO | WO-2010/071852 A2 | 6/2010 |

(Continued)

OTHER PUBLICATIONS

Liu et al. Structure-based programming of lymph-node targeting in molecular vaccines. Nature. Mar. 27, 2014, vol. 507, pp. 519-522. (Year: 2014).*
Appelbe et al., "Radiation-enhanced delivery of systemically administered amphiphilic-CpG oligodeoxynucleotide," J Control Release. 266:248-255 (2017).
Extended European Search Report for European Patent Application No. 19761384.7, dated Nov. 16, 2021 (9 pages).
International Preliminary Report on Patentability for International Patent Application No. PCT/US2019/020398, issued Sep. 8, 2020 (6 pages).

(Continued)

*Primary Examiner* — Jeffrey E. Russel
(74) *Attorney, Agent, or Firm* — Clark & Elbing LLP

(57) ABSTRACT

The invention provides compounds including a CpG oligodeoxynucleotide sequence linked to a lipid by a linker and related compositions and methods. The invention features a compound consisting of the nucleotide sequence of SEQ ID NO:1, at its 5' end, bonded or linked by a linker to a lipid. Further, the invention features a method of treating a cancer in a human patient, comprising administering to the patient the compound. Further, the invention features a pharmaceutical composition including the compound and a pharmaceutically acceptable carrier. The invention features a kit including (I) the compound or a composition comprising the compound; and (ii) a protein comprising SEQ ID NO:2 or SEQ ID NO:3.

14 Claims, 10 Drawing Sheets
Specification includes a Sequence Listing.

(56) References Cited

FOREIGN PATENT DOCUMENTS

| WO | WO-2016040887 A2 * | 3/2016 | ............. A61K 39/12 |
| WO | WO-2018/102584 A1 | 6/2018 | |

OTHER PUBLICATIONS

International Preliminary Report on Patentability for International Patent Application No. PCT/US2019/020404 issued Sep. 8, 2020 (4 pages).
International Search Report for International Patent Application No. PCT/US2019/020398, mailed Jun. 13, 2019 (4 pages).
International Search Report for International Patent Application No. PCT/US2019/020404, mailed Jun. 24, 2019 (4 pages).
Liu et al., "Membrane anchored immunostimulatory oligonucleotides for in vivo cell modification and localized immunotherapy," Angew Chem Int Ed Engl. 50(31):7052-5 (2011) (12 pages).
Written Opinion of the International Searching Authority for International Patent Application No. PCT/US2019/020398, mailed Jun. 13, 2019 (5 pages).
Written Opinion of the International Searching Authority for International Patent Application No. PCT/US2019/020404, mailed Jun. 24, 2019 (3 pages).
Yu et al., "Immunostimulatory Properties of Lipid Modified CpG Oligonucleotides," Mol Pharm. 14(8):2815-2823 (2017).
Examination Report for Saudi Arabian Patent Application No. 520420065 dated Feb. 27, 2022 (9 pages).
Written Opinion for Singaporean Patent Application No. 11202008432X dated Feb. 21, 2022 (5 pages).
Examination Report for Saudi Arabian Patent Application No. 520420065 dated Jan. 31, 2023 (6 pages).
Notice of Deficiencies for Israeli Patent Application No. 277101, dated Mar. 1, 2023 (3 pages).
Notice of Reasons for Refusal for Japanese Patent Application No. 2020-568945 mailed Feb. 14, 2023 (6 pages).
Office Action for Chinese Patent Application No. 201980028828.9, issued Apr. 21, 2023 (12 pages).
Wang et al., "In vitro and in vivo evaluations of human papillomavirus type 16 (HPV16)-derived peptide-loaded dendritic cells (DCs) with a CpG oligodeoxynucleotide (CpG-ODN) adjuvant as tumor vaccines for immunotherapy of cervical cancer," Arch Gynecol Obstet. 289(1):155-62 (Epub Aug. 2013).
You et al., Chapter 24: Drug chemical structure modification and new drug research and development. Medicinal Chemistry, Second Edition. The Medical Science and Technology Press of China, 570-572 (Feb. 2011) (7 pages).
Zhang et al., Chapter 5: Design of Drugs Acting on Nucleic Acids. Modern Drug Design, First Edition. The Medical Science and Technology Press of China, 272 (Dec. 2005) (5 pages).
Office Action and Search Report for Russian Patent Application No. 2020132295, issued Sep. 7, 2022 (16 pages).
Marciani, D. J., "Vaccine adjuvants: role and mechanisms of action in vaccine immunogenicity," Drug Discov Today. 8(20):934-43. (Oct. 2003).
De Vries et al. "Drug delivery systems based on nucleic acid nanostructures," Journal of Controlled Release. 172: 467-483. Dec. 2013. (19 pages).

* cited by examiner

CPG AMPHIPHILES AND USES THEREOF

SEQUENCE LISTING

The instant application contains a Sequence Listing which has been submitted electronically in ASCII format and is hereby incorporated by reference in its entirety. Said ASCII copy, created on Aug. 26, 2020 is named 51026-027002 Sequence Listing 8.26.20 ST25 and is 4,993 bytes in size.

BACKGROUND OF THE INVENTION

Human papillomavirus (HPV)-related cancer is one of the fastest growing cancers in the world. Overall, 5% of all cancers world-wide can be attributed to HPV infections. There continues to be a need for further and more effective cancer treatments.

SUMMARY OF THE INVENTION

The invention provides compounds that can be used in therapeutic methods.

Accordingly, in the first aspect, the invention features a compound consisting of the nucleotide sequence 5'-TCGTCGTTTTGTCGTTTTGTCGTT-3' (SEQ ID NO:1), at its 5' end, bonded or linked by a linker to the following lipid:

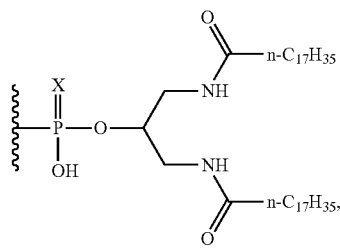

or a salt thereof,
where X is O or S.

In one embodiment of the first aspect of the invention, the nucleotide sequence is bonded to the lipid.

In another embodiment of the first aspect of the invention, all internucleoside groups connecting the nucleosides in 5'-TCGTCGTTTTGTCGTTTTGTCGTT-3' (SEQ ID NO:1) are phosphorothioates.

In the second aspect, the invention features a method of treating a cancer in a human patient. This method includes administering to the patient the compound of the first aspect of the invention, a protein including the amino acid sequence:
MHQKRTAMFQ DPQERPRKLP QLCTELQTTI HDII-LECVYC KQQLLRREVY DFAFRDLCIV YRDGNPYAVG DKCLKFYSKI SEYRHYCYSL YGTTLEQQYN KPLCDLLIRC INGQKPLCPE EKQRHLDKKQ RFHNGRGRWT GRCMSCCRSS RTRRETQL (SEQ ID NO:2), and a protein including the amino acid sequence: MHGDTPTLHE YMLDLQ-PETT DLYGYGQLND SSEEEDEIDG PAGQAE-PDRA HYNIVTFCCK CDSTLRLCVQ STHVDIRTLE DLLMGTLGIV CPICSQKP (SEQ ID NO:3).

In one embodiment of the second aspect of the invention, the cancer is human papillomavirus (HPV) positive (e.g., HPV type 16 positive).

In another embodiment of the second aspect of the invention, the cancer is a head or neck squamous cell carcinoma.

In an additional embodiment of the second aspect of the invention, the patient is receiving or has received platinum-containing chemotherapy. In a further embodiment, an anti-PD-1 antibody (e.g., pembrolizumab or nivolumab) is administered to the patient.

In another embodiment of the second aspect of the invention, the compound of the first aspect of the invention and the proteins including the amino acid sequences of SEQ ID NO:2 and SEQ ID NO:3 are administered concurrently.

In a further embodiment of the second aspect of the invention, the compound of the first aspect of the invention and the proteins including the amino acid sequences of SEQ ID NO:2 and SEQ ID NO:3 are administered sequentially.

In a further aspect, the invention features another method of treating a cancer in a human patient. This method includes administering to the patient the compound of the first aspect of the invention, a protein including the amino acid sequence:
MHQKRTAMFQ DPQERPRKLP QLCTELQTTI HDII-LECVYC KQQLLRREVY DFAFRDLCIV YRDGNPYAVG DKCLKFYSKI SEYRHYCYSL YGTTLEQQYN KPLCDLLIRC INGQKPLCPE EKQRHLDKKQ RFHNGRGRWT GRCMSCCRSS RTRRETQL (SEQ ID NO:2), a protein including the amino acid sequence: MHGDTPTLHE YMLDLQ-PETT DLYGYGQLND SSEEEDEIDG PAGQAE-PDRA HYNIVTFCCK CDSTLRLCVQ STHVDIRTLE DLLMGTLGIV CPICSQKP (SEQ ID NO:3), and an anti-PD-1 antibody (e.g., pembrolizumab or nivolumab).

In the third aspect, the invention features a pharmaceutical composition including a compound of the first aspect of the invention and a pharmaceutically acceptable carrier.

In one embodiment of the third aspect, the pharmaceutical composition further includes a protein including the amino acid sequence: MHQKRTAMFQ DPQERPRKLP QLCTELQTTI HDIILECVYC KQQLLRREVY DFAFRDLCIV YRDGNPYAVG DKCLKFYSKI SEY-RHYCYSL YGTTLEQQYN KPLCDLLIRC INGQKPLCPE EKQRHLDKKQ RFHNGRGRWT GRCMSCCRSS RTRRETQL (SEQ ID NO:2), and a protein including the amino acid sequence:

```
                                           (SEQ ID NO: 3)
MHGDTPTLHE YMLDLQPETT DLYGYGQLND SSEEEDEIDG

PAGQAEPDRA HYNIVTFCCK CDSTLRLCVQ STHVDIRTLE

DLLMGTLGIV CPICSQKP.
```

In the fourth aspect, the invention features a kit including (i) a compound of the first aspect of the invention or a composition of the second aspect of the invention and (ii) a protein including the amino acid sequence: MHQKR-TAMFQ DPQERPRKLP QLCTELQTTI HDIILECVYC KQQLLRREVY DFAFRDLCIV YRDGNPYAVG DKCLKFYSKI SEYRHYCYSL YGTTLEQQYN KPLCDLLIRC INGQKPLCPE EKQRHLDKKQ RFHN-GRGRWT GRCMSCCRSS RTRRETQL (SEQ ID NO:2), and a protein including the amino acid sequence: MHGDTPTLHE YMLDLQPETT DLYGYGQLND SSEEEDEIDG PAGQAEPDRA HYNIVTFCCK CDSTLRLCVQ STHVDIRTLE DLLMGTLGIV CPICSQKP (SEQ ID NO:3).

3

Definitions

A "linker," as used herein, refers to a monovalent or divalent group, in which one valency is covalently bonded to one biologically functional group, and the other valency is covalently bonded to another biologically functional group. In one example, a linker connects a nucleotide sequence of, e.g., a CpG oligonucleotide, to a lipid (e.g., —P(X)(OH)—O—CH(CH$_2$NHCO—(CH$_2$)$_{16}$—CH$_3$)$_2$, or a salt thereof, where X is O or S, as described herein). Such linkers can optionally include one or more nucleotides, for example, a dinucleotide (e.g., GG).

A "pharmaceutically acceptable carrier," as used herein, refers to a vehicle capable of suspending or dissolving the active compound, and having the properties of being non-toxic and non-inflammatory in a patient. Moreover, a pharmaceutically acceptable carrier may include a pharmaceutically acceptable additive, such as a preservative, antioxidant, fragrance, emulsifier, dye, or excipient known or used in the field of drug formulation and that does not significantly interfere with the therapeutic effectiveness of the biological activity of the active agent, and that is non-toxic to the patient.

The terms "treat," "treatment," and "treating" refer to therapeutic approaches in which the goal is to reverse, alleviate, ameliorate, inhibit, slow down, or stop the progression or severity of a condition associated with a disease or disorder, e.g., cancer. These terms include reducing or alleviating at least one adverse effect or symptom of a condition, disease, or disorder. Treatment is generally "effective" if one or more symptoms or clinical markers are reduced, or if a desired response (e.g., a specific immune response) is induced. Alternatively, treatment is "effective" if the progression of a disease is reduced or halted.

The invention provides several advantages. For example, in including lipid moieties and, optionally, a linker, certain compounds of the invention bind to endogenous albumin in subjects to whom they are administered, which enhances delivery of the compounds to the lymph nodes of the subjects. This facilitates the induction of a therapeutic immune response against, for example, HPV proteins administered to the subject, leading to effective cancer treatment.

Other features and advantages of the invention will be apparent from the following detailed description, the drawings, and the claims.

DETAILED DESCRIPTION OF THE INVENTION

Figure 1:
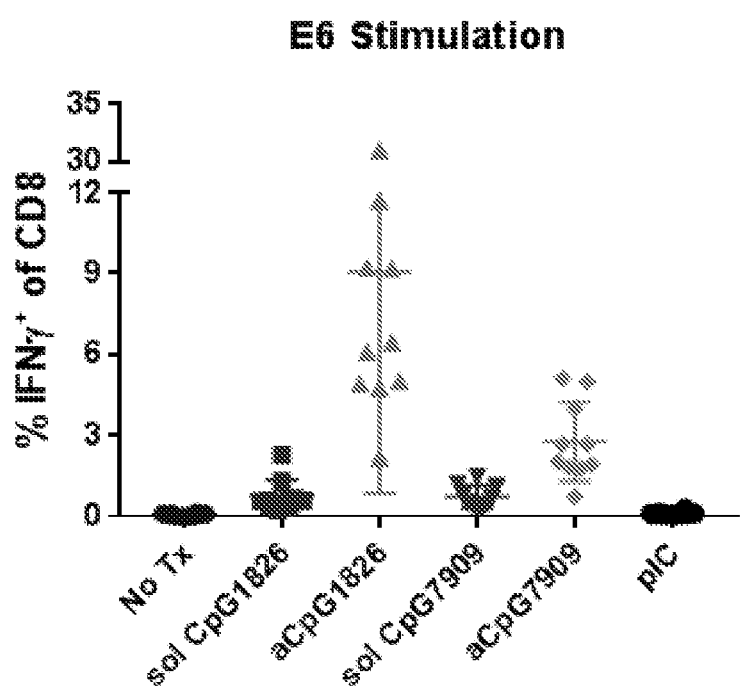
FIG. 1 is a graph showing the immune response against HPV16 E6.

The invention provides compounds that can be used in therapeutic methods. The compounds include CpG oligodeoxynucleotides (ODNs) (e.g., a CpG ODN having the sequence 5'-TCGTCGTTTTGTCGTTTTGTCGTT-3' (SEQ ID NO:1)). The CpG ODN is linked, at its 5' end, to a lipid, such as the following:

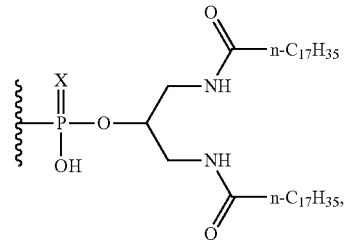

or a salt thereof, where X is O or S. Preferably, X is S. The CpG oligonucleotide may be directly bonded to the lipid. Alternatively, the CpG may be linked to the lipid through a linker, such as GG. In the CpG oligonucleotide, all internucleoside groups are phosphorothioates (e.g., all internucleoside groups in the compound may be phosphorothioates).

The CpG ODN can function as an adjuvant to elicit an immune response in a subject, such as an immune response against a cancer antigen (e.g., a HPV antigen). As such, the compounds and compositions of the invention can be used in therapeutic methods. In particular, if the CpG ODN containing compound is administered in combination with one or more HPV proteins the compound can induce an immune response to HPV positive cancer cells. Accordingly, the invention provides methods of treating cancer in a subject (e.g., a human patient) by administering one or more compounds or compositions of the invention to the subject. In various examples, the cancer is a HPV positive (e.g., a HPV type 16 positive) cancer.

The HPV positive cancer may be a head or neck squamous cell carcinoma, a cervical cancer, anal cancer, vulvar cancer, head and neck cancer, oropharyngeal cancer, penile cancer, vaginal cancer, virally induced cancer, bladder cancer, pancreatic cancer, lung cancer, liver cancer, ovarian cancer, colon cancer, stomach cancer, neuroblastoma, breast cancer, prostate cancer, renal cancer, leukemia, sarcoma, carcinoma, basal cell carcinoma, non-small cell lung carcinoma, non-Hodgkin's lymphoma, acute myeloid leukemia (AML), chronic lymphocytic leukemia (CLL), B-cells chronic lymphocytic leukemia (B-CLL), multiple myeloma (MM), erythroleukemia, renal cell carcinoma, sarcoma, melanoma, astrocytoma, oligoastrocytoma, biliary tract cancer, choriocarcinoma, CNS cancer, larynx cancer, small cell lung cancer, non-small cell lung cancer (NSCLC), adenocarcinoma, giant (or oat) cell carcinoma, squamous cell carcinoma, oral cavity cancer, skin cancer, basal cell cancer, squamous cell cancer, testicular cancer, thyroid cancer, uterine cancer, rectal cancer, a cancer of the respiratory system, or a cancer of the urinary system.

Optionally, the methods of the invention can further include administering a compound or composition of the invention in combination with a second (or further) different approach to treatment.

The invention also provides kits that each contain, for example, a first vessel that includes one or more compounds of the invention, optionally together with a second vessel that includes a cancer antigen, such as an HPV protein described herein.

CpG

CpG ODNs are short synthetic single-stranded DNA molecules containing unmethylated CpG dinucleotides in particular sequence contexts. CpG ODNs possess a partially or completely phosphorothioated (PS) backbone, as opposed to the natural phosphodiester (PO) backbone in DNA molecules. Three major classes of stimulatory CpG ODNs have been identified based on structural characteristics and activity on human peripheral blood mononuclear cells (PBMCs), in particular B cells and plasmacytoid dendritic cells (pDCs). These three classes are Class A (Type D), Class B (Type K), and Class C.

CpG1826 and CpG7909 both are in CpG class B. Class B CpG ODNs contain a full PS backbone with one or more CpG dinucleotides. They strongly activate B cells and TLR9-dependent NF-κB signaling but weakly stimulate IFN-α secretion.

Mutated HPV

Point mutations at C70G, C113G, and I135G (underlined below) can be introduced into the wild-type HPV16 E6 viral protein to prevent stereochemical interaction with human p53. The performance of this component as an antigen is dictated by the sequence of the protein, with the structure of the protein being inconsequential to that intended function.

```
mHPV 16 E6
                              (158 aa; SEQ ID NO: 2)
MHQKRTAMFQ DPQERPRKLP QLCTELQTTI HDIILECVYC

KQQLLRREVY DFAFRDLCIV YRDGNPYAVG DKCLKFYSKI

SEYRHYCYSL YGTTLEQQYN KPLCDLLIRC INGQKPLCPE

EKQRHLDKKQ RFHNGRGRWT GRCMSCCRSS RTRRETQL
```

Point mutations at C24G and E26G (underlined below) can be introduced into the wild-type HPV16 E7 viral protein to prevent stereochemical interaction with human Rb1. Again, the performance of this component as an antigen is dictated by the sequence of the protein, with the structure of the protein being inconsequential to that intended function.

```
mHPV 16 E7
                              (98 aa; SEQ ID NO: 3)
MHGDTPTLHE YMLDLQPETT DLYGYGQLND SSEEEDEIDG

PAGQAEPDRA HYNIVTFCCK CDSTLRLCVQ STHVDIRTLE

DLLMGTLGIV CPICSQKP.
```

CpG ODNs may be bonded directly or linked by a linker to the lipid. These compounds may be produced using the ordinary phosphoramidite chemistry known in the art. In some examples, the CpG ODN or CpG ODN-GG may be reacted with the following compound:

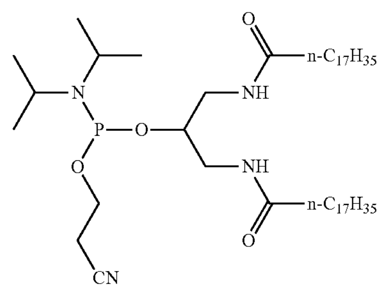

to produce an intermediate, which upon oxidation with (e.g., phosphite oxidation methods known in the art, e.g., a sulfurizing agent, such as 3-((N,N-dimethylaminomethylidene)amino)-3H-1,2,4-dithiazole-5-thione) and hydrolysis of the cyanoethyl group may produce a compound of the invention.

In order that this invention be more fully understood, the following examples are set forth. These examples are for the purpose of illustration only and are not to be construed as limiting the scope of the invention in any way.

EXAMPLES

Example 1: HPV16 E6 and HPV16 E7 Proteins in Combination with a CpG Amphiphile Adjuvant Generates an Immune Response Mice were immunized prophylactically and the immune response generated was recorded via E7-Tetramer stain and IFNγ-intracellular cytokine staining (ICS) upon HPV16 E6 and HPV16 E7 (E6/E7) stimulation.

The experimental design included the following 6 groups of mice (n=10 for each group)

1. No immunization
2. E6/E7+soluble CpG1826
3. E6/E7+amphiphile CpG1826 (aCpG1826)
4. E6/E7+soluble CpG7909
5. E6/E7+amphiphile CpG7909 (aCpG7909; FIG. 14)
6. E6/E7+polyIC (pIC)

pIC was used as a benchmark adjuvant control.

Protein stock solutions were dissolved in 8M urea. Adjuvant stock solutions are dissolved in $H_2O$. Final injections are diluted with 1× phosphate buffered saline (PBS) (CF of urea <1 M).

For aCpG1826, the sequence used was the soluble CpG1826 sequence (5'-tccatgacgttcctgacgtt-3'; SEQ ID NO:4) with two guanines added at the 5' end (5'-ggtccatgacgttcctgacgtt-3'; SEQ ID NO:5). A concentration of 5 nmol for each 100 μl injection was used for both soluble CpG1826 and aCpG1826. CpG1826 is an optimal mouse sequence while CpG7909 is optimal for humans and poorly active in mice. CpG1826 and CpG7909 are in the same CpG class (class B) and generally have similar activity profiles in their respective species.

For both aCpG7909 and soluble CpG7909, the sequence used was 5'-tcgtcgttttgtcgttttgtcgtt-3' (SEQ ID NO:6) at a concentration of 5 nmol for each 100 μl injection.

Mutated HPV16 E6 with point mutations at C70G, C113G, and I135G (underlined below) was used for immunization. The amino acid sequence used is provided below.

```
mHPV 16 E6
                             (158 aa; SEQ ID NO: 2)
MHQKRTAMFQ DPQERPRKLP QLCTELQTTI HDIILECVYC

KQQLLRREVY DFAFRDLCIV YRDGNPYAVG DKCLKFYSKI

SEYRHYCYSL YGTTLEQQYN KPLCDLLIRC INGQKPLCPE

EKQRHLDKKQ RFHNGRGRWT GRCMSCCRSS RTRRETQL
```

Mutated HPV16 E7 with point mutations at C24G and E26G (underlined below) was used for immunization. The amino acid sequence used is provided below.

```
mHPV 16 E7
                              (98 aa; SEQ ID NO: 3)
MHGDTPTLHE YMLDLQPETT DLYGYGQLND SSEEEDEIDG

PAGQAEPDRA HYNIVTFCCK CDSTLRLCVQ STHVDIRTLE

DLLMGTLGIV CPICSQKP
```

For E6/E7, 10 μg each of mutated HPV16 E6 and mutated HPV16 E7 was used per 100 μl injection.

Female C57BL/6J mice (B6) were immunized subcutaneously (s.c.) with the primer dose (E6/7+aCpG) and one booster dose after 2 weeks.

Figure 3:
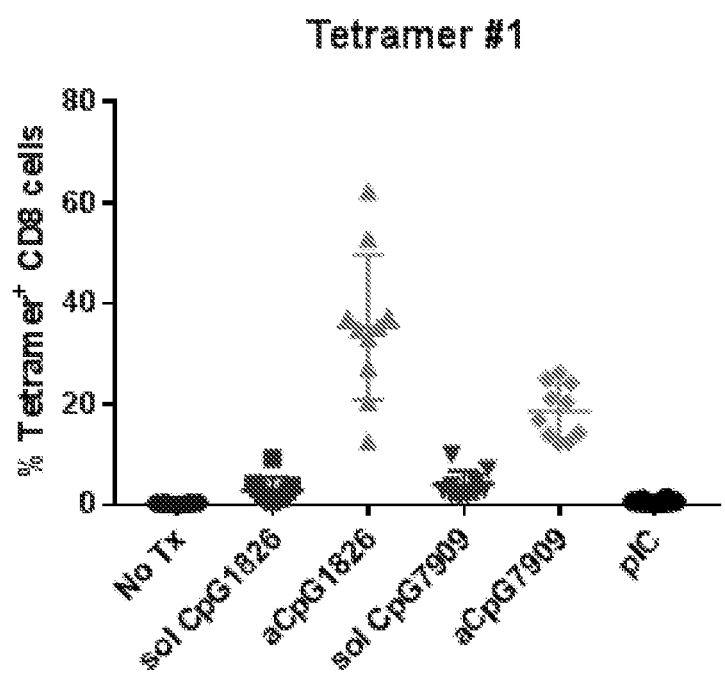
FIG. 3 is a graph showing tetramer stain analysis for HPV16 E7.

Tetramer analysis for H-2Db HPV16 E7 (RAHYNIVTF; SEQ ID NO:7) was performed 7 days after the booster dose (FIG. 3).

Intracellular cytokine staining (ICS) for IFNγ was performed on peripheral blood 7 days after the booster dose to analyze immune responses to E6/E7.

The E6 stimulation used the following peptides: (E6-10: EVYDFAFRDL (SEQ ID NO:8); E6 49-57: VYDFAFRDL (SEQ ID NO:9); E6 37-45: CVYCKQQLL; (SEQ ID NO:10); E6 72-80: KCLKFYSKI (SEQ ID NO:11); and E6 100-108: NKPLCDLLI (SEQ ID NO:12) to generate the data shown in FIG. 1.

Deconvolution of the E6 stimuli revealed that E49-57 was the only peptide that resulted in stimulation.

For E7 stimulation the following peptide was used: RAHYNIVTF (SEQ ID NO:13). This peptide was used to generate the data shown in FIG. 2.

Figure 2:
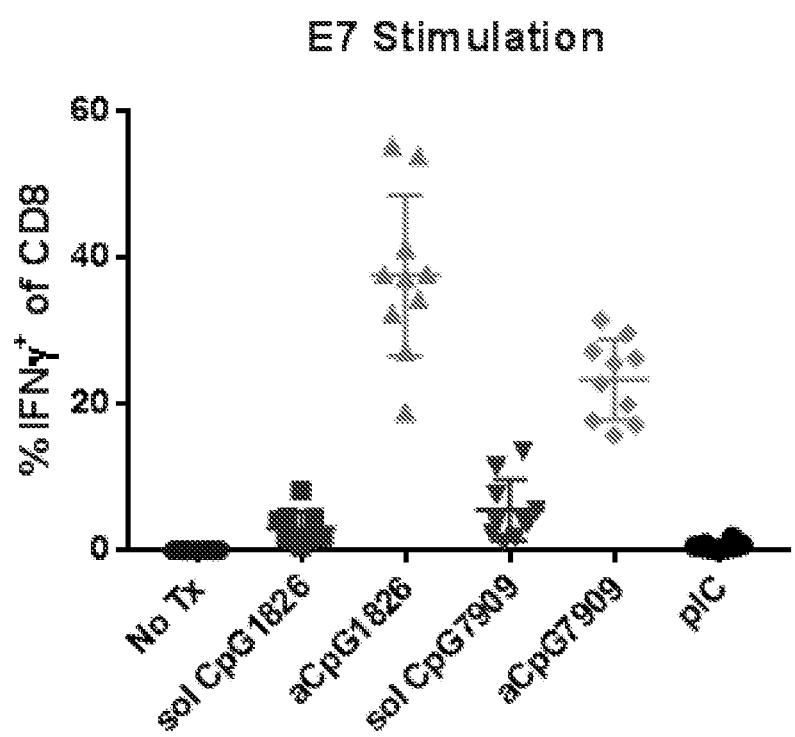
FIG. 2 is a graph showing the immune response against HPV16 E7.

As shown in FIGS. 1 and 2, use of aCpG1826 generated a strong immune response against both mutant HPV16 E6 and mutant HPV16 E7.

As also shown in FIGS. 1 and 2, use of aCpG7909, which is optimal for humans and generally performs poorly in mice, surprisingly generated a strong immune response against both mutant HPV16 E6 and mutant HPV16 E7.

Figure 4:
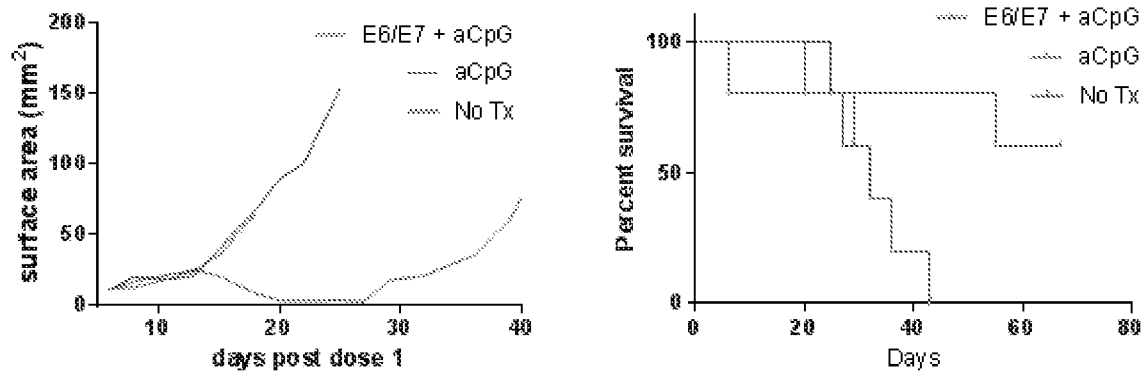
FIG. 4 is a series of graphs showing that administration of HPV16 E6 and HPV16 E7 with an amphiphile-CpG (aCpG) decreased tumor size compared to aCpG alone or no treatment (No Tx).

E6/E7+aCpG decreased tumor growth compared to either aCpG alone or no treatment with a corresponding increase in percent survival (FIG. 4).

Example 2: Determination of a Dosing Schedule for HPV 16 E7 and aCPG

To determine an optimal dosing schedule for E7+aCpG with respect to anti-tumor efficacy in female C57BL/6U (B6) mice implanted with TC-1 tumors, weekly dosing was compared to dosing every 2 weeks and to baseline (prime only). E7+aCpG was compared to E7+soluble CpG. All vaccines were administered 3 times (prime and 2 boosts).

Female C57BL/6J mice (B6) were inoculated with 50,000 TC-1 cells subcutaneously in the flank on Day 0 and 12 days later; mice were separated into treatment groups and treated as indicated in Table 1.

TABLE 1

| Test Article | Dose[a] | Dosing Interval | Injection Volume (ROA) | N | Endpoints |
|---|---|---|---|---|---|
| NA | 0 | Untreated Control | NA | 10 | Serum cytokines Anti-E7 serum antibodies Tetramer analysis for H-2Db HPV16 E7 Tumor size Survival |
| E7 + aCpG | 10 μg E7 1.24 nmol aCpG-1826[b] | Single Dose | 100 μL, divided (SC) | 10 | Serum cytokines Anti-E7 serum antibodies |
| | | Weekly | 100 μL, divided (SC) | 20 | Tetramer analysis for H-2Db HPV16 E7 |
| | | Every 2 Weeks | 100 μL, divided (SC) | 20 | Tumor size Survival |
| E7 + CpG | 10 μg E7 1.24 nmol CpG-1826 | Single Dose | 100 μL, divided (SC) | 10 | Anti-E7 serum antibodies Tetramer analysis for H- |
| | | Weekly | 100 μL, divided (SC) | 20 | 2Db HPV16 E7 Tumor size |
| | | Every 2 Weeks | 100 μL, divided (SC) | 20 | Survival |

[a]Protein stock solutions were dissolved in 8M urea. Adjuvant stock solutions were dissolved in $H_2O$. Final injections were diluted with 1X PBS ($C_F$ of urea <1M).
[b]8 μg equivalent
NA = not applicable;
PBS = phosphate-buffered saline;
ROA = route of administration;
SC = subcutaneous Throughout the study tumor sizes were measured every other day up to Day 40 post inoculation and animal survival was monitored. Tetramer analysis for H-2Db HPV16 E7 (RAHYNIVTF) was performed 7 days after each vaccine administration.

Serum samples were taken 1 hour and 4 hours after each vaccine administration for the aCpG groups and analyzed via cytometric bead array for cytokine expression (IFNγ, TNFα, IL-6, IL-10, IL-12p70, MCP-1).

Anti-E7 serum antibody titers were analyzed 14 days after initial vaccination. ELISA plates were coated with whole protein E7, upon which serum antibodies were captured and detected with anti-Fc antibody.

Figure 5:
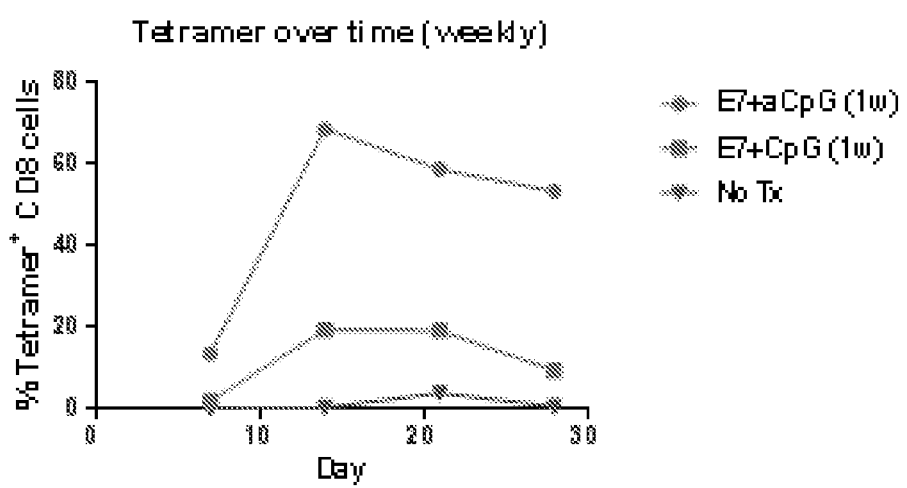
FIG. 5 is a graph showing superior HPV tetramer response with aCpG vaccine compared with soluble CpG vaccine at different time points.
Figure 6:
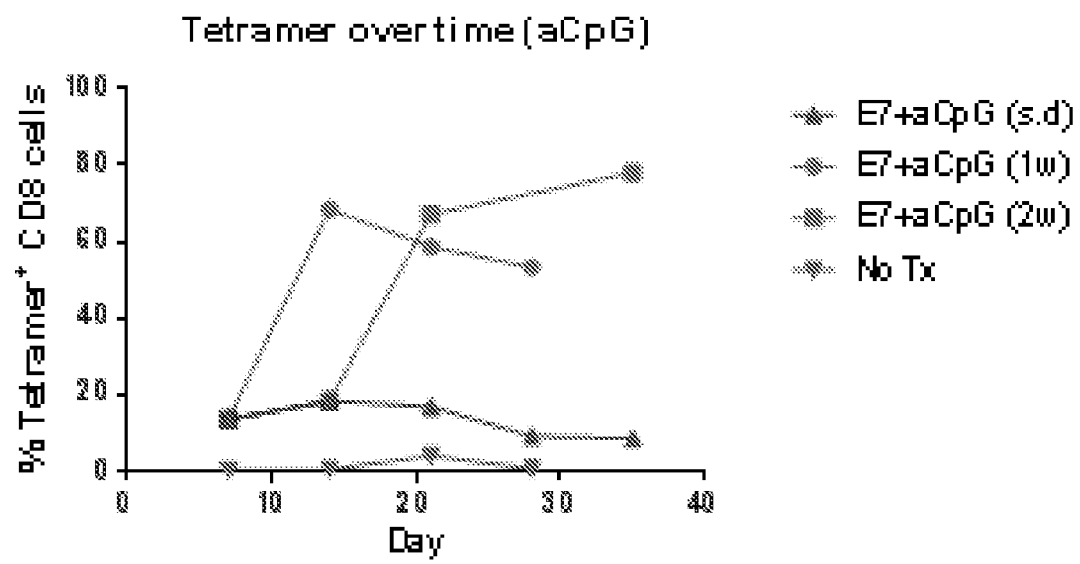
FIG. 6 is a graph showing sustained HPV tetramer responses over time with aCpG administered once weekly or once every two weeks.
Figure 7:
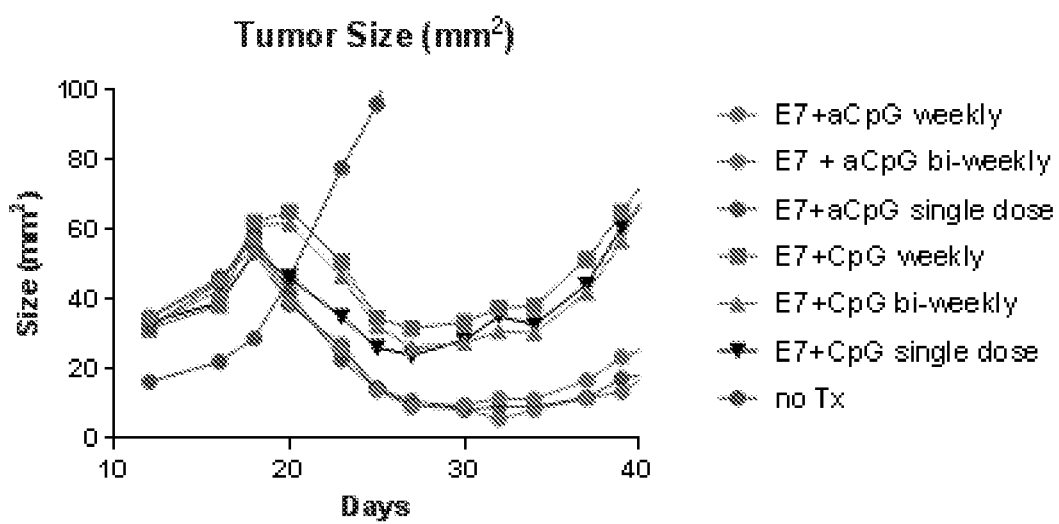
FIG. 7 is a graph showing tumor size response to E7 vaccine treatment.
Figure 8:
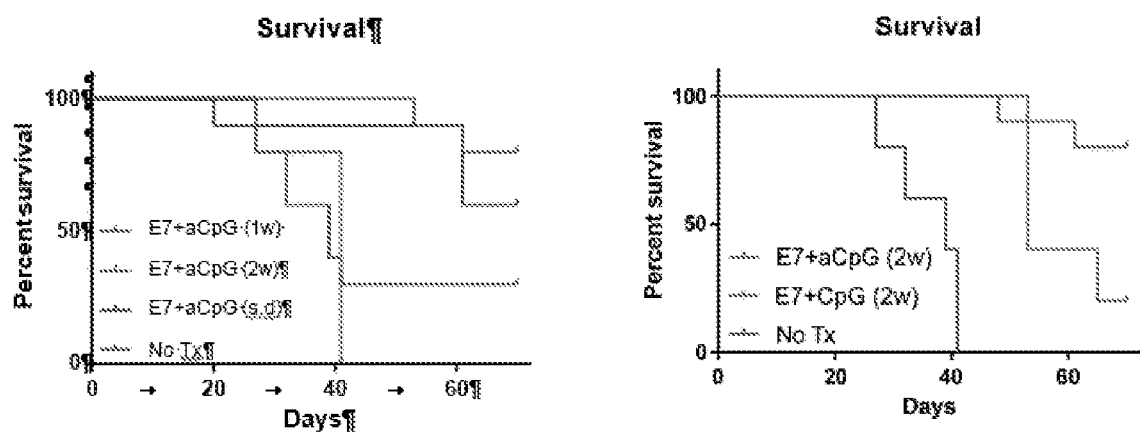
FIG. 8 is a graph showing improved survival in E7-vaccine treated C57BL6 mice implanted with TC-1 tumor cells.
Figure 9:
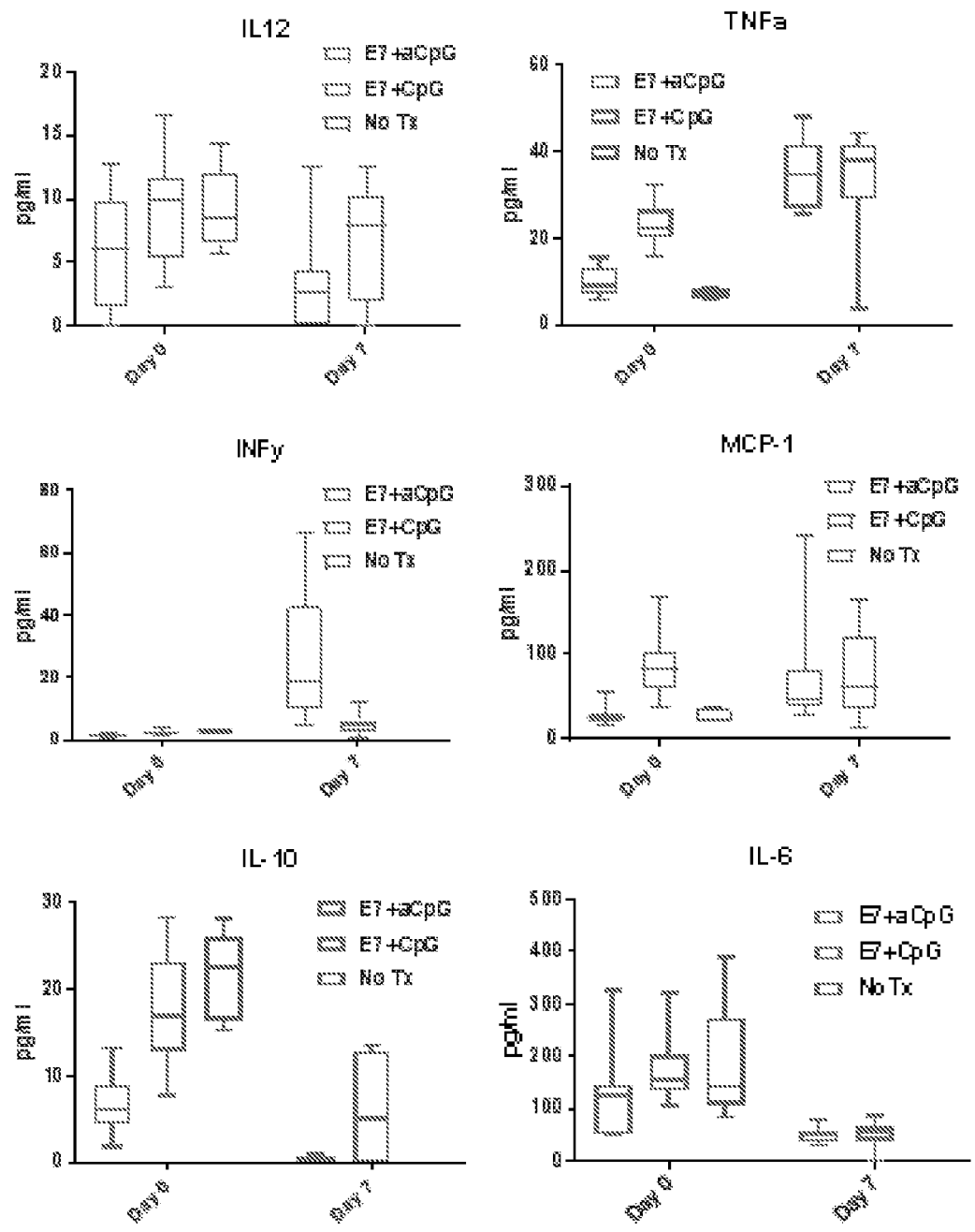
FIG. 9 is a series of graphs showing serum cytokine level changes after dosing.

The HPV-tetramer specific T cell response to the protein/amphiphilic CpG vaccine was superior to that of the protein/soluble CpG vaccine after both a single dose and repeated doses (FIG. 5). The HPV-tetramer response to protein/aCpG was increased further after administration of boost vaccinations, and the increases were sustained out to Days 28 and 35 (FIG. 6) for the once weekly and once every 2 weeks regimens, respectively. The strong HPV-tetramer response in the aCpG groups correlated to reductions in tumor size compared to animals vaccinated with soluble CpG (FIG. 7) and improved survival (FIG. 8). Treatment-related increases in systemic cytokines were comparable between soluble and aCpG groups except for IL-10, which was lower for aCpG compared to soluble CpG, and IFNγ which was higher for aCpG compared to soluble CpG (FIG. 9).

Example 3: Antitumor Efficacy of E7 Protein in Combination with Either Soluble or Amphiphilic CpG and With or Without the Addition of an Anti-PD-1 Antibody To evaluate the antitumor efficacy of E7 protein in combination with either soluble or amphiphilic CpG and with or without the addition of an anti-PD-1 antibody, female C57BL/6J mice (B6) were inoculated in the flank at baseline with 50,000 TC-1 cells. Eleven days post-inoculation the mice were divided into 5 groups as shown in Table 2. The comparison group was untreated.

TABLE 2

| Test Article | Dose[a] | Dosing Interval | Injection Volume (ROA) | N | Endpoints |
| --- | --- | --- | --- | --- | --- |
| NA | 0 | Untreated Control | NA | 10 | Tumor size every other day up to Day 40 Survival Tetramer analysis for H-2Db HPV16 E7 (RAHYNIVTF peptide; SEQ ID NO: 13) 7 days after each vaccine administration |
| E7 + CpG | 10 μg E7 1.24 nmol CpG-1826 | Every 2 Weeks | 100 μL, divided (SC) | 10 | |
| E7 + aCpG | 10 μg E7 1.24 nmol aCpG-1826 | Every 2 Weeks | 100 μL, divided (SC) | 10 | |
| E7 + CpG + PD-1 antibody | 10 μg E7 1.24 nmol CpG-1826 230 μL anti-PD-1 | Every 2 Weeks for both vaccine and antibody | 100 μL, divided (SC) Antibody IP (100 μL divided) | 10 | |
| E7 + aCpG + PD-1 antibody | 10 μg E7 1.24 nmol aCpG-1826 230 μL anti-PD-1 | Every 2 Weeks For both vaccine and antibody | 100 μL, divided (SC) Antibody IP (100 μL divided) | 10 | |

[a]Protein stock solutions were dissolved in 8M urea. Adjuvant stock solutions were dissolved in $H_2O$.

Final injections were diluted with 1X PBS ($C_F$ of urea <1M).

IP = intraperitoneal;

NA = not applicable;

PBS = phosphate-buffered saline;

ROA = route of administration;

SC = subcutaneous

Throughout the study tumor sizes were measured every other day up to day 40 post inoculation and animal survival was monitored. Tetramer analysis for H-2Db HPV16 E7 (RAHYNIVTF) was performed 7 days after each vaccine administration.

Figure 10:
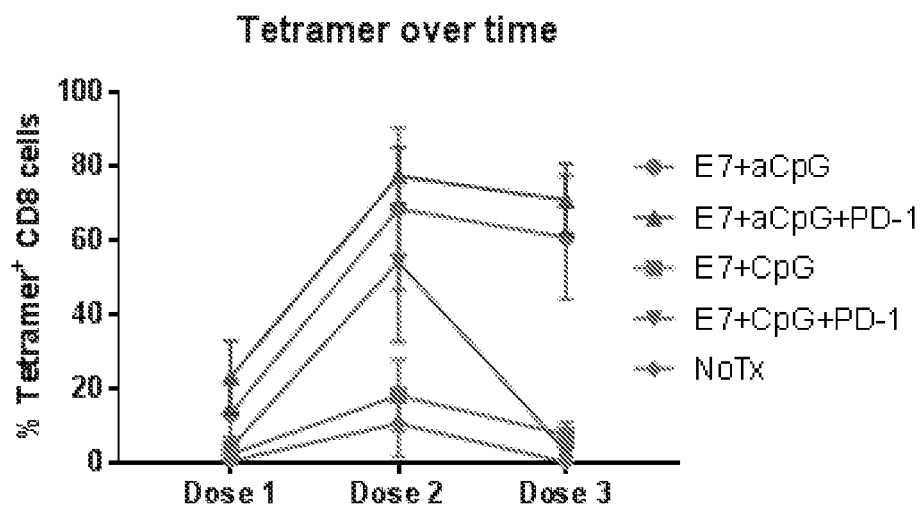
FIG. 10 is a graph showing tetramer responses over time for an HPV16 E7/aCpG vaccine.

Administration of E7/Amph-CpG vaccine, without or without anti-PD-1 antibody, caused a robust increase in HPV Tetramer+CD8-cells specific to the HPV16 E7 (RAHYNIVTF; SEQ ID NO:13) peptide (FIG. 10). These responses were clearly visible as early as after the first dose, peaked on the 2nd dose, and were sustained out to the 3rd dose (in contrast to the lower responses observed with E7/CpG, which though increased by concomitant administration of anti-PD-1 were not sustained.

Figure 11:
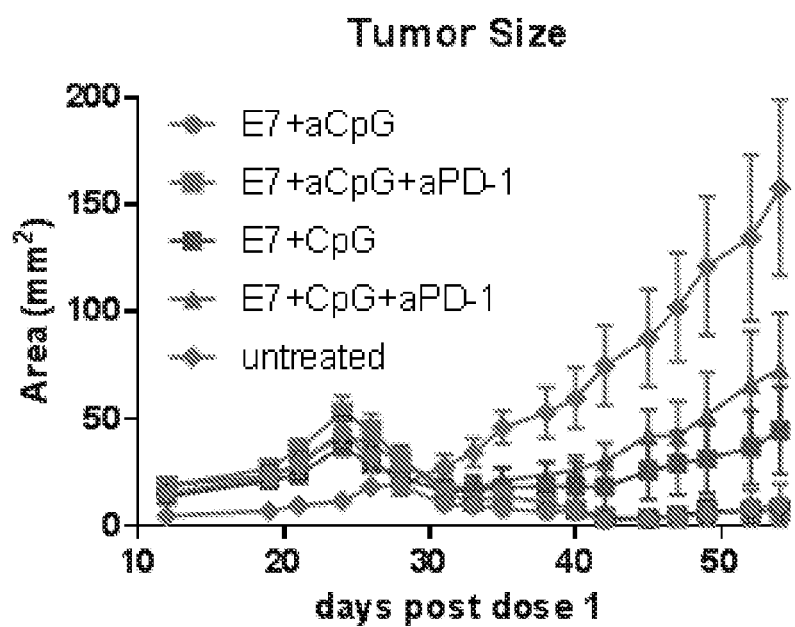
FIG. 11 is a graph showing tumor growth response to HPV16 E7/aCpG vaccination plus or minus administration of an anti-PD-1 antibody.

Corresponding to these strong HPV Tetramer+CD8 responses, tumor growth was halted around Day 24 and reversed after the first dose of E7/Amph-CpG (with or without anti-PD-1) and tumor size remained small and stable out to the end of the study, in contrast to the other groups where growth progressed (FIG. 11).

Figure 12:
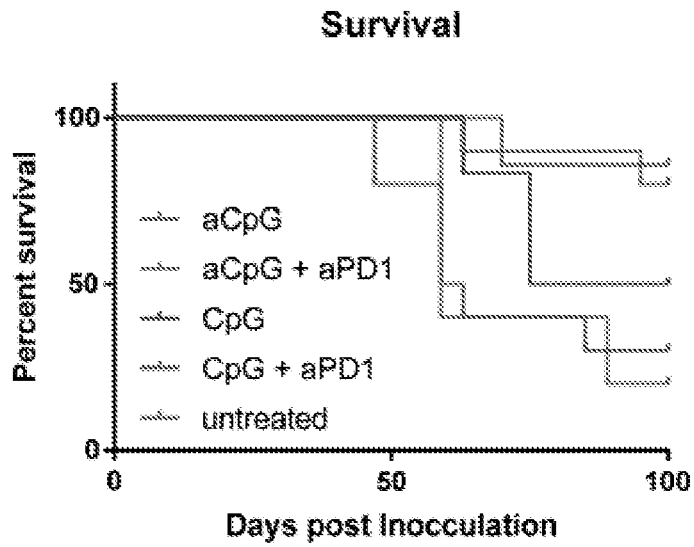
FIG. 12 is a graph showing the effects of HPV16 E7/aCpG vaccination plus or minus administration of an anti-PD-1 antibody on survival in TC-1 tumor bearing mice.

Also, corresponding to the effects on tumor size, treatment with E7/aCpG vaccine (with or without the anti-PD-1 antibody) had a significant effect on survival and resulted in 6/7 (85%) cures for E7/aCpG without antibody and 8/10 (80%) cures for E7/aCpG plus anti-PD-1 antibody (FIG. 12).

Example 4: aCpG Dose Escalation Study

To determine a dose of aCpG that produces the highest antigen-specific Tetramer+CD8 response over the course of 6 doses, a dose escalation study was conducted using a fixed dose of 10 μg ovalbumin (OVA) as the antigen. Soluble CpG was used as a comparator. Tolerability (based on body weight and general observations) was also assessed. The study design is outlined in Table 3.

TABLE 3

| Antigen/Dose | Adjuvant | Adjuvant Dose (nmol) | ROA (Dose Volume) |
|---|---|---|---|
| OVA 10 μg | Amph-CpG-1826 | 0.12 | SC (100 μL, divided) |
| | | 0.60 | |
| | | 1.2 | |
| | | 6 | |
| | | 12 | |
| | Soluble CpG-1826 | 1.2 | |
| | | 6 | |
| | | 12 | |
| | | 60 | |

ROA = route of administration;
SC = subcutaneous

Up to 6 doses of vaccine were administered at 2-week intervals for a total study length of 11 weeks.

Peripheral blood samples were collected 7 days after each injection and flow cytometric analyses of tetramer on CD8+ cells were performed using H-2KbOVA (SIINFEKL; SEQ ID NO:14).

Figure 13:
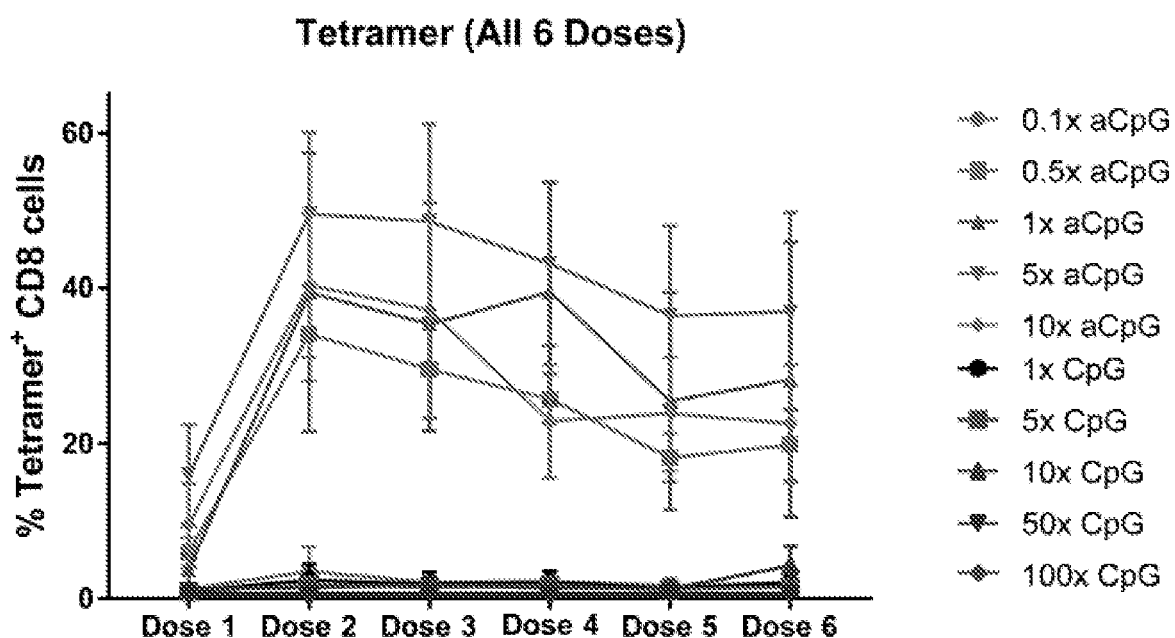
FIG. 13 is a graph showing tetramer analysis for aCpG dose escalation.
Figure 14:
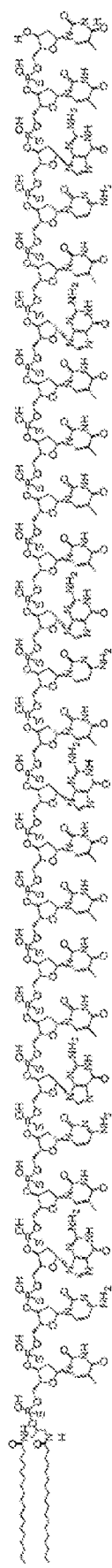
FIG. 14 shows the structure of amphiphile-CpG-7909; 5'-(Diacyl lipid) TCG TCG TTT TGT CGT TTT GTC GTT-3' (SEQ ID NO:1). All bases are DNA. All linkages are phosphoramidite, including the link between the diacyl lipid and the oligodeoxynucleotide.

Significant increases in tetramer+CD8+cells were observed only in the groups treated with aCpG+OVA, with 6 nmol producing the greatest pharmacological effect (FIG. 13). No weight loss, loss of interest/appetite, or wounds/lesions were observed.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety.

Some embodiments of the invention are within the following numbered paragraphs.

1. A compound consisting of the nucleotide sequence 5'-TCGTCGTTTTGTCGTTTTGTCGTT-3' (SEQ ID NO:1), at its 5' end, bonded or linked by a linker to the following lipid:

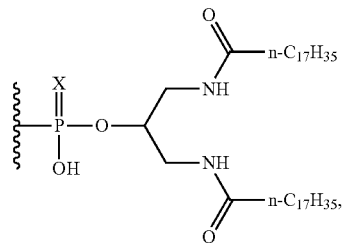

or a salt thereof,
wherein X is O or S.

2. The compound of paragraph 1, wherein the nucleotide sequence is bonded to the lipid.
3. The compound of paragraph 1 or 2, wherein all internucleoside groups connecting the nucleosides in 5'-TCGTCGTTTTGTCGTTTTGTCGTT-3' (SEQ ID NO:1) are phosphorothioates.
4. A method of treating a cancer in a human patient comprising administering to the patient the compound of any one of paragraphs 1 to 3, a protein comprising the amino acid sequence:

```
                                       (SEQ ID NO: 2)
MHQKRTAMFQ DPQERPRKLP QLCTELQTTI HDIILECVYC

KQQLLRREVY DFAFRDLCIV YRDGNPYAVG DKCLKFYSKI

SEYRHYCYSL YGTTLEQQYN KPLCDLLIRC INGQKPLCPE

EKQRHLDKKQ RFHNGRGRWT GRCMSCCRSS RTRRETQL,
``` and a protein comprising the amino acid sequence:

```
                                       (SEQ ID NO: 3)
MHGDTPTLHE YMLDLQPETT DLYGYGQLND SSEEEDEIDG

PAGQAEPDRA HYNIVTFCCK CDSTLRLCVQ STHVDIRTLE

DLLMGTLGIV CPICSQKP.
```

5. The method of paragraph 4, wherein the cancer is human papillomavirus (HPV) positive.
6. The method of paragraph 5, wherein the cancer is HPV type 16 positive.
7. The method of any one of paragraphs 4 to 6, wherein the cancer is a head or neck squamous cell carcinoma.

8. The method of any one of paragraphs 4 to 7, wherein the patient is receiving or has received platinum-containing chemotherapy.

9. The method of paragraph 4, wherein the compound of paragraph 1 and the proteins comprising the amino acid sequences of SEQ ID NO:2 and SEQ ID NO:3 are administered concurrently.

10. The method of paragraph 4, wherein the compound of paragraph 1 and the proteins comprising the amino acid sequences of SEQ ID NO:2 and SEQ ID NO:3 are administered sequentially.

11. A pharmaceutical composition comprising a compound of any one of paragraphs 1 to 3 and a pharmaceutically acceptable carrier.

12. The pharmaceutical composition of paragraph 11, wherein the composition further comprises a protein comprising the amino acid sequence:

```
                                          (SEQ ID NO: 2)
MHQKRTAMFQ DPQERPRKLP QLCTELQTTI HDIILECVYC

KQQLLRREVY DFAFRDLCIV YRDGNPYAVG DKCLKFYSKI

SEYRHYCYSL YGTTLEQQYN KPLCDLLIRC INGQKPLCPE

EKQRHLDKKQ RFHNGRGRWT GRCMSCCRSS RTRRETQL,
``` and a protein comprising the amino acid sequence:

```
                                          (SEQ ID NO: 3)
MHGDTPTLHE YMLDLQPETT DLYGYGQLND SSEEEDEIDG

PAGQAEPDRA HYNIVTFCCK CDSTLRLCVQ STHVDIRTLE

DLLMGTLGIV CPICSQKP.
```

13. A kit comprising (i) a compound of any one of paragraphs 1 to 3 or a composition of paragraph 11 and (ii) a protein comprising the amino acid sequence:

```
                                          (SEQ ID NO: 2)
MHQKRTAMFQ DPQERPRKLP QLCTELQTTI HDIILECVYC

KQQLLRREVY DFAFRDLCIV YRDGNPYAVG DKCLKFYSKI

SEYRHYCYSL YGTTLEQQYN KPLCDLLIRC INGQKPLCPE

EKQRHLDKKQ RFHNGRGRWT GRCMSCCRSS RTRRETQL,
``` and a protein comprising the amino acid sequence:

```
                                          (SEQ ID NO: 3)
MHGDTPTLHE YMLDLQPETT DLYGYGQLND SSEEEDEIDG

PAGQAEPDRA HYNIVTFCCK CDSTLRLCVQ STHVDIRTLE

DLLMGTLGIV CPICSQKP.
```

Other embodiments are within the following claims.

What is claimed is:

1. A compound consisting of the nucleotide sequence 5'-TCGTCGTTTTGTCGTTTTGTCGTT-3' (SEQ ID NO:1), at its 5' end, bonded or linked by a linker to the following lipid:

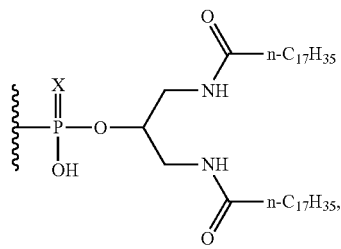

or a salt thereof, wherein X is O or S, and wherein the nucleotides in the nucleotide sequence are optionally joined by one or more phosphorothioate bonds.

2. The compound of claim 1, wherein the nucleotide sequence is bonded to the lipid.

3. The compound of claim 1, wherein all internucleoside groups connecting the nucleosides in 5'-TCGTCGTTTTGTCGTTTTGTCGTT-3' (SEQ ID NO:1) are phosphorothioates.

4. A method of treating a human papillomavirus (HPV) positive cancer in a human patient comprising administering to the patient the compound of claim 1, a protein comprising the amino acid sequence:

(SEQ ID NO: 2)
MHQKRTAMFQ DPQERPRKLP QLCTELQTTI HDIILECVYC

KQQLLRREVY DFAFRDLCIV YRDGNPYAVG DKCLKFYSKI

SEYRHYCYSL YGTTLEQQYN KPLCDLLIRC INGQKPLCPE

EKQRHLDKKQ RFHNGRGRWT GRCMSCCRSS RTRRETQL, and a protein comprising the amino acid sequence:

(SEQ ID NO: 3)
MHGDTPTLHE YMLDLQPETT DLYGYGQLND SSEEEDEIDG

PAGQAEPDRA HYNIVTFCCK CDSTLRLCVQ STHVDIRTLE

DLLMGTLGIV CPICSQKP.

5. The method of claim 4, wherein the cancer is HPV type 16 positive.

6. The method of claim 4, wherein the cancer is a head or neck squamous cell carcinoma.

7. The method of claim 4, wherein the patient is receiving or has received platinum-containing chemotherapy.

8. The method of claim 4, wherein the compound and the proteins comprising the amino acid sequences of SEQ ID NO:2 and SEQ ID NO:3 are administered concurrently.

9. The method of claim 4, wherein the compound and the proteins comprising the amino acid sequences of SEQ ID NO:2 and SEQ ID NO:3 are administered sequentially.

10. A pharmaceutical composition comprising a compound of claim 1 and a pharmaceutically acceptable carrier.

11. The pharmaceutical composition of claim 10, wherein the composition further comprises a protein comprising the amino acid sequence:

(SEQ ID NO: 2)
MHQKRTAMFQ DPQERPRKLP QLCTELQTTI HDIILECVYC

KQQLLRREVY DFAFRDLCIV YRDGNPYAVG DKCLKFYSKI

SEYRHYCYSL YGTTLEQQYN KPLCDLLIRC INGQKPLCPE

EKQRHLDKKQ RFHNGRGRWT GRCMSCCRSS RTRRETQL, and a protein comprising the amino acid sequence:

(SEQ ID NO: 3)
MHGDTPTLHE YMLDLQPETT DLYGYGQLND SSEEEDEIDG

PAGQAEPDRA HYNIVTFCCK CDSTLRLCVQ STHVDIRTLE

DLLMGTLGIV CPICSQKP.

12. A kit comprising (i) a compound of claim 1, and (ii) a protein comprising the amino acid sequence:

(SEQ ID NO: 2)
MHQKRTAMFQ DPQERPRKLP QLCTELQTTI HDIILECVYC
KQQLLRREVY DFAFRDLCIV YRDGNPYAVG DKCLKFYSKI
SEYRHYCYSL YGTTLEQQYN KPLCDLLIRC INGQKPLCPE
EKQRHLDKKQ RFHNGRGRWT GRCMSCCRSS RTRRETQL, and a protein comprising the amino acid sequence:

(SEQ ID NO: 3)
MHGDTPTLHE YMLDLQPETT DLYGYGQLND SSEEEDEIDG
PAGQAEPDRA HYNIVTFCCK CDSTLRLCVQ STHVDIRTLE
DLLMGTLGIV CPICSQKP.

13. A method of treating a human papillomavirus (HPV) positive cancer in a human patient comprising administering to the patient the compound of claim 2, a protein comprising the amino acid sequence:

(SEQ ID NO: 2)
MHQKRTAMFQ DPQERPRKLP QLCTELQTTI HDIILECVYC
KQQLLRREVY DFAFRDLCIV YRDGNPYAVG DKCLKFYSKI
SEYRHYCYSL YGTTLEQQYN KPLCDLLIRC INGQKPLCPE
EKQRHLDKKQ RFHNGRGRWT GRCMSCCRSS RTRRETQL, and a protein comprising the amino acid sequence:

(SEQ ID NO: 3)
MHGDTPTLHE YMLDLQPETT DLYGYGQLND SSEEEDEIDG
PAGQAEPDRA HYNIVTFCCK CDSTLRLCVQ STHVDIRTLE
DLLMGTLGIV CPICSQKP.

14. The compound of claim 2, wherein all internucleoside groups connecting the nucleosides in 5'-TCGTCGTTTTGTCGTTTTGTCGTT-3' (SEQ ID NO:1) are phosphorothioates.

* * * * *

SEQUENCE LISTING

```
<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: Synthetic Construct

<400> SEQUENCE: 1
tcgtcgtttt gtcgttttgt cgtt                                           24

<210> SEQ ID NO 2
<211> LENGTH: 158
<212> TYPE: PRT
<213> ORGANISM: Artificial Sequence
<220> FEATURE:
<223> OTHER INFORMATION: Synthetic Construct

<400> SEQUENCE: 2

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Gly Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95
```

Gln Gln Tyr Asn Lys Pro Leu Cys Asp Leu Leu Ile Arg Cys Ile Asn
            100                 105                 110

Gly Gln Lys Pro Leu Cys Pro Glu Glu Lys Gln Arg His Leu Asp Lys
        115                 120                 125

Lys Gln Arg Phe His Asn Gly Arg Gly Arg Trp Thr Gly Arg Cys Met
130                 135                 140

Ser Cys Cys Arg Ser Ser Arg Thr Arg Arg Glu Thr Gln Leu
145                 150                 155

<210> SEQ ID NO 3
<211> LENGTH: 98
<212> TYPE: PRT
<213> ORGANISM: Artificial Sequence
<220> FEATURE:
<223> OTHER INFORMATION: Synthetic Construct

<400> SEQUENCE: 3

Met His Gly Asp Thr Pro Thr Leu His Glu Tyr Met Leu Asp Leu Gln
1               5                   10                  15

Pro Glu Thr Thr Asp Leu Tyr Gly Tyr Gly Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
tccatgacgt tcctgacgtt                                             20

<210> SEQ ID NO 5
<211> LENGTH: 22
<212> TYPE: DNA
<213> ORGANISM: Artificial Sequence
<220> FEATURE:
<223> OTHER INFORMATION: Synthetic Construct

<400> SEQUENCE: 5
ggtccatgac gttcctgacg tt                                          22

<210> SEQ ID NO 6
<211> LENGTH: 24
<212> TYPE: DNA
<213> ORGANISM: Artificial Sequence
<220> FEATURE:
<223> OTHER INFORMATION: Synthetic Construct

<400> SEQUENCE: 6
tcgtcgtttt gtcgttttgt cgtt                                        24

```
<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Arg Ala His Tyr Asn Ile Val Thr Phe
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct

<400> SEQUENCE: 8

Glu Val Tyr Asp Phe Ala Phe Arg Asp Leu
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Synthetic Construct

<400> SEQUENCE: 9

Val Tyr Asp Phe Ala Phe Arg Asp Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

Cys Val Tyr Cys Lys Gln Gln Leu Leu
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11

Lys Cys Leu Lys Phe Tyr Ser Lys Ile
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Asn Lys Pro Leu Cys Asp Leu Leu Ile
1               5
```

```
<210> SEQ ID NO 13
<211> LENGTH: 9
<212> TYPE: PRT
<213> ORGANISM: Artificial Sequence
<220> FEATURE:
<223> OTHER INFORMATION: Synthetic Construct

<400> SEQUENCE: 13

Arg Ala His Tyr Asn Ile Val Thr Phe
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Construct

<400> SEQUENCE: 14

Ser Ile Ile Asn Phe Glu Lys Leu
1               5
```